(12) United States Patent
Bell

(10) Patent No.: US 6,755,802 B2
(45) Date of Patent: Jun. 29, 2004

(54) WHOLE BLOOD SAMPLING DEVICE

(75) Inventor: Michael L. Bell, Fullerton, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 46 days.

(21) Appl. No.: 10/139,569

(22) Filed: May 6, 2002

(65) Prior Publication Data
US 2003/0206828 A1 Nov. 6, 2003

(51) Int. Cl.[7] .................. A61M 37/00; A61B 19/00; B01D 27/00; B65D 81/00; G01N 1/00
(52) U.S. Cl. .............. 604/6.15; 604/6.04; 604/403; 604/405; 210/437; 210/448; 600/576; 435/287.3; 73/863; 73/863.21; 73/863.24
(58) Field of Search .............. 604/4.01, 6.01, 604/6.04, 6.07, 6.15, 403, 405–6, 411, 415–16, 317; 210/644, 649–51, 348, 406, 435, 437–39, 446, 448, 500.1, 500.21–500.24; 422/100–1, 104; 73/863, 863.21, 863.23, 863.81, 864, 864.01–864.02, 864.11, 864.21, 864.91, 864.81–864.87; 435/283.1, 287.1, 287.3, 297.1–297.4; 436/174, 177–78, 68; 424/520, 529–30

(56) References Cited

U.S. PATENT DOCUMENTS

| | | | |
|---|---|---|---|
| 3,830,106 A | 8/1974 | Gardiner et al. | 73/421 B |
| 3,954,623 A * | 5/1976 | Hammer et al. | 210/436 |
| 4,162,896 A | 7/1979 | Hosli | 23/230 R |
| 4,385,637 A | 5/1983 | Akhavi | 128/763 |
| 4,396,024 A | 8/1983 | Sarstedt | 128/763 |
| 4,624,929 A | 11/1986 | Ullman | 436/179 |
| 4,693,820 A * | 9/1987 | Baxter | 210/232 |
| 4,812,293 A | 3/1989 | McLaurin et al. | 422/69 |
| 5,264,184 A | 11/1993 | Aysta et al. | 422/101 |
| 5,919,356 A | 7/1999 | Hood | 210/85 |
| 6,241,886 B1 * | 6/2001 | Kitagawa et al. | 210/507 |

* cited by examiner

Primary Examiner—Patricia Bianco
(74) Attorney, Agent, or Firm—Sheldon & Mak; Kristin C. Hübner; Jeffrey G. Sheldon

(57) ABSTRACT

A portable hand-held blood sampling device having a self-filling capability includes a blood separation filter. The filter has a plurality of pores sized to permit passage of selected blood constituents such as blood plasma through the device. The device has a separated blood conduit that extends beyond the outlet of the device and is shaped for easy penetration into a self-sealing septum of a blood analyzer. An annular shield extends from the device outlet beyond the conduit to prevent inadvertent contact of the conduit by a user.

27 Claims, 2 Drawing Sheets

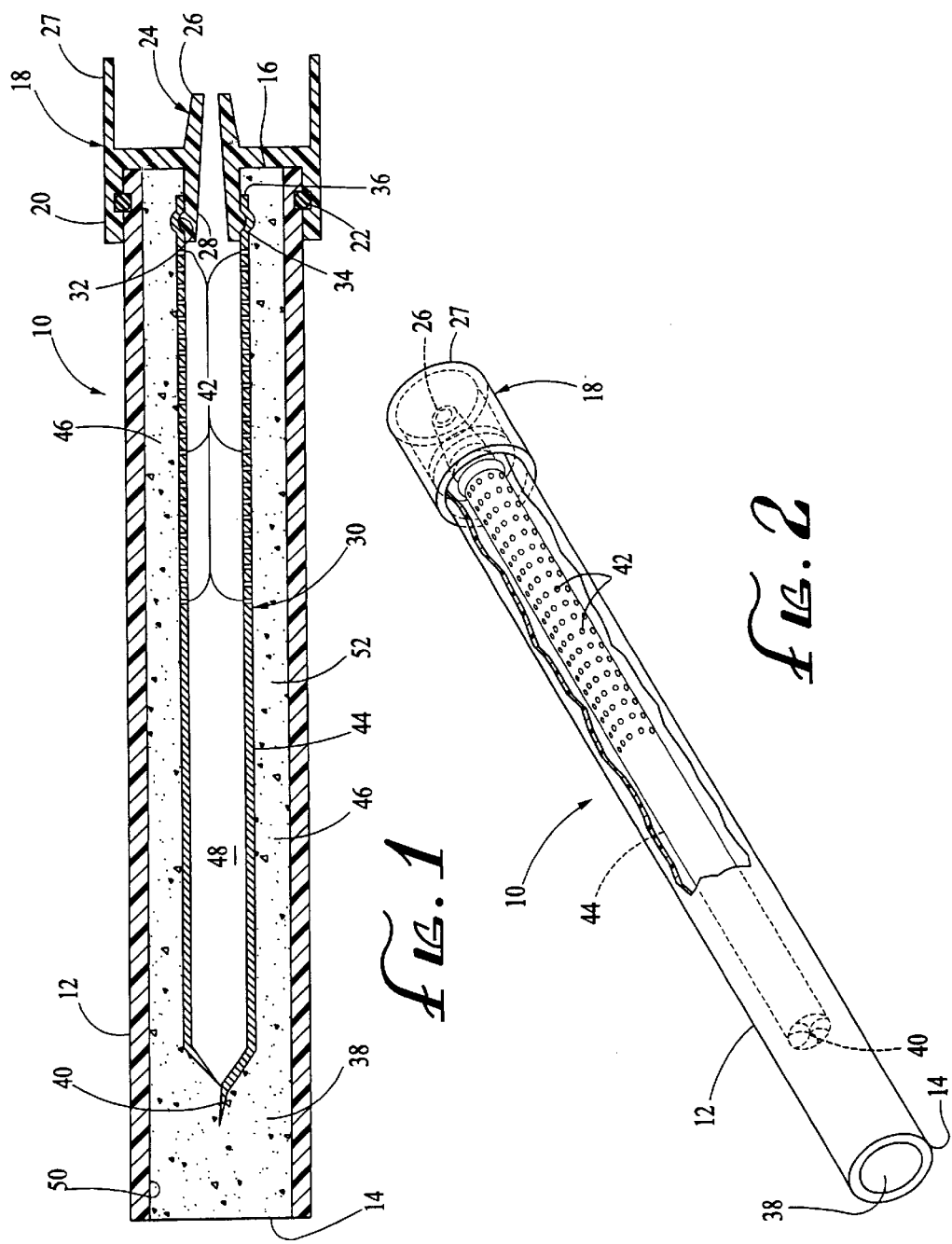

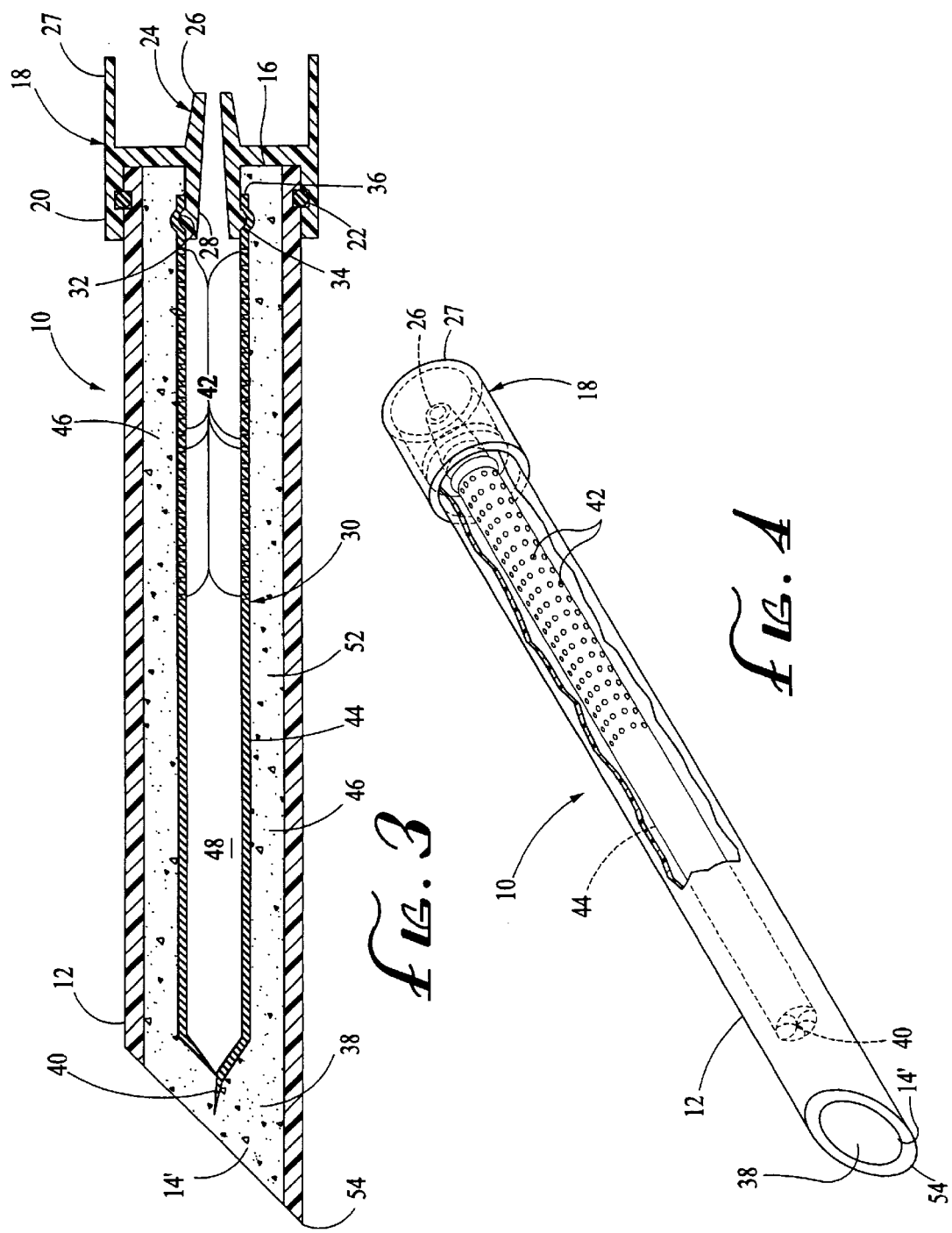

WHOLE BLOOD SAMPLING DEVICE

FIELD OF THE INVENTION

The present invention relates to portable hand-held devices for extracted blood elements, such as blood plasma, from whole blood.

BACKGROUND OF THE INVENTION

The use of blood sampling devices is known in the art. Typically, blood samples are taken from a patient utilizing a finger stick or draw tube. As is recognized in the art, the obtained sample is difficult to analyze. For example, the sample contains a variable proportion of cells which affect the quantization of analytes measured in non-equilibrium assays. The blood sample is subject to clotting with the end result of clogging the small channels in typical blood analyzers. The blood sample contains fragile blood cells that, if ruptured, can alter the concentration of some analytes. Moreover, a very high number of blood cells could overwhelm the read capability of an analyzer that is cytometer-based. Some sampling devices known in the art, such as, for example, described in U.S. Pat. No. 5,919,356, utilize a needle that is insertable into a patient to draw blood, by pulling a plunger of a syringe, which then flows into a chamber that contains membrane fibers. Filtration through the membrane is accomplished by either shaking the device or by depressing the plunger of the syringe. The separated sample is contained in a collector chamber. Devices of this type are not intended for use with a blood analyzer. Moreover, the devices of the prior art, such as described above, require puncturing the skin of a patient by way of a needle/syringe arrangement to extract an unnecessarily large volume of blood from the patient. This presents a potential trauma affect on patients sensitive to needle punctures of their skin. The present invention serves to remedy the shortcomings of the prior art.

SUMMARY OF THE INVENTION

The present invention is directed to a device for collecting a blood sample that is to be analyzed by the use of a blood analyzer. The device comprises a hollow fluid tight tube having an inlet opening for receiving a blood sample and a separation filter in the tube that serves to separate out desired blood constituents for later analysis. Such a constituent is blood plasma and the filter is hollow and contains a plurality of pores sized to prevent whole blood and blood cells from passage into the hollow part of the filter while providing passage of blood plasma through the filter. The tube has a wettable surface and the relative size of the filter within the tube provides for self-filling capability of the device through capillary action, thus providing self-filling capability combined with a blood separation filter in one device. The device includes a conduit that extends from the filter to the outlet of the device. The conduit is a stent-like structure that has a tapered end for easy penetration into a septum of an analyzer that acts as a self-closing sample inlet channel in the analyzer manifold. Annularly disposed about the outlet of the device is a shield that extends away from the outlet a distance greater than the separated blood conduit. The shield protects the conduit from inadvertent contact by the user of the device. This protects the sample from any contamination by a user and prevents the user from contact with a contaminated sample.

In practice, a droplet of blood is introduced at the device inlet and by virtue of the combined affects of the wettable interior surface of the tube and the interior fill volume, blood is drawn into the device under capillary action into the device. The device is placed on an analyzer such that the separated blood conduit pierces the inlet channel septum whereupon a vacuum is drawn by the analyzer to draw the blood sample through separation filter thereby introducing the separated blood, i.e., blood plasma, into the analyzer.

As an alternate embodiment of the present invention, the inlet of the device may be formed with a sharp projection to act as a blood drawing lancet and the shield may be in the form of an anchoring device, such as a Luer Lock. As a result of the aforementioned features, the present invention is characterized as being a point of need clinical analyzer; that is compact and portable; that provides a small volume of plasma in a relatively short period of time; that is relatively inexpensive compared to traditional blood draw disposables; that protects the operator from contact with potentially infectious sample; and lastly does not require a dedicated piece of equipment to separate plasma from cells.

BRIEF DESCRIPTION OF THE DRAWINGS

FIG. 1 is a cross-sectional view of an embodiment of the present invention;

FIG. 2 is a partial cut-away perspective view of the embodiment of FIG. 1;

FIG. 3 is an alternate embodiment of the invention of FIG. 1; and

FIG. 4 is a partial cut-away perspective view of the embodiment of FIG. 3.

DETAILED DESCRIPTION

Referring now to the drawings, there is shown an embodiment of the blood sampling device of the present invention. More specifically, FIGS. 1 and 3 show a device 10 formed of a hollow cylindrical tube 12 having an inlet end 14 and an outlet end 16. The tube 12 may be manufactured of any one of a number of conventional materials, such as rigid plastic known in the art. The outlet end 16 includes an end cap 18 that is anchored to the tube 12 in fluid tight fashion. The end cap 18 may be anchored to the tube 12 for example, by means of a fluid insoluble adhesive and the like. The end cap 18 has an overlap portion 20 that circumferentially overlaps the outlet 16 and a fluid sealing O-ring 22 is positioned annularly between the tube 12 and the overlap portion 20 in respective recesses so as to provide further fluid sealing at the outlet 16. Although the cap 18 is shown as part of the device assembly, it is to be understood that the cap 18 may be made integrally as part of the tube 12 and such is within the contemplation of the present invention.

The end cap 18 includes a relatively small stent-like conduit 24 that extends across the boundary defined by the tube outlet 16 to a station immediately beyond the outlet 16. The portion 26 of stent 24 beyond the outlet 16, has a somewhat conical profile to, as will be discussed later, facilitate penetration of the stent 24 into a self-closing sample inlet channel of a blood sample analyzer manifold. An annular shield 27 extends outward from end cap 18 to a station beyond the distal end of the stent conical portion 26. The shield 27 reduces the potential of inadvertent contact of the stent 24 during handling of the device 10 so as to maintain the stent 24 free of contamination during use and avoid user contact with a contaminated sample.

The stent portion 28 extends interiorly of the tube 12 a distance sufficient to provide mating engagement with filter 30. The stent portion 28 includes an outwardly extending annular lobe 32 dimensioned to securely fit within filter annular recess 34 located proximate to the filters distal end 36. The filter 30 may be anchored to the stent portion 28 by means of a press-fit arrangement or by use of adhesives known in the art. The device inlet 14 defines an inlet chamber 38 and the filter 30 extends essentially the length of the interior of tube 12 from between the end cap 18 into inlet chamber 38. The filter 30 has a generally tubular shape having a circular cross-section, a closed end 40 and an open end 36 that is, as described above, mounted on stent portion 28 in fluid tight relationship. The filter 30 is formed of a membrane that is naturally impervious to the passage of whole blood and as shown in FIGS. 2 and 4, has a plurality of pores 42 disposed along and around filter wall 44. The region 46 between the filter 30 and the interior of the tube 12 including the inlet chamber 38 defines a fill volume that holds whole blood that is introduced at the inlet 14. The pores 42 extend through filter wall 44 and are sized to limit the flow of only blood plasma through the filter walls 44 and into the filter interior 48. The pore size may be about 2 micrometers in diameter and preferably in the range of about 0.1 to 1.0 micrometers. As will be discussed later, the process of drawing plasma into the filter interior 48 and out of the device 10 through stent 24 is under the aspiration action of an external blood analyzer. The pores 42 lie in a region starting at the filter distal end 36 and progresses toward the closed end 40 a distance that corresponds to about half of the initial blood fill volume. The tube 12 has an interior wall 50 conditioned to have a wettable lumenal surface. The cross-sectional area of the tube 12 is sized such that, in combination with the wettable surface characteristics of the interior wall 50, the device is self-filling by capillary action. In that regard, the volume of the tube is sized to be in the range of about 0.5 milliliter and the internal diameter of the tube is in the range of about 1 millimeter. Accordingly, when the device is full of blood, the weight associated with the blood is less than about 5 grams. The filter 30 is essentially cylindrical and sized such that the volume immediately surrounding the filter should be entirely sheathed in blood, even if the amount of blood is insufficient to completely fill the tube 12. To prevent clotting of blood contained within the tube 12, an anti-coagulant reagent 52, preferably in dry form, is dispersed throughout the interior of the tube 12. In such manner, the flow of blood plasma from the tube 12 through the filter 30 is facilitated.

In practice, use of the device in combination with a blood analyzer is as follows. A droplet of blood is introduced at the device inlet end 14, an aliquot of blood enters tube 12 under the influence of capillary action. Upon entry into tube 12, the blood dissolves the anti-coagulant 52 that inhibits the clotting of the blood. Because of the self-filling nature of the device 10, sample retention within the tube 12 is maintained irrespective of the device orientation. Subsequent to introducing the sample in tube 12, a device user inserts the end cap 18 into the sampling port of a blood analyzer. The stent portion 26 penetrates a self-closed inlet channel in the analyzer manifold. Typical self-closing techniques and apparatus utilize a pierced septum of a compliant material, such as silicone rubber. Once the device 10 is inserted into the sampling port of the analyzer, the analyzer pump aspirates through sample inlet 14 to develop a negative pressure with respect to ambient. The negative pressure pulls plasma from the blood sample in tube 12, through the pores 42 and into the filter interior 48 and finally into the analyzer manifold. No additional venting is needed for this operation as the sampling device 10 is vented through inlet 14. The aspirated sample is preceded by a variable amount of air. The analyzer pump dispenses the first portion of the sample to waste to dispose of this air. Once an adequate sample has been aspirated, the analyzer routes wash fluid around and through stent 24 within the tube 12 to remove droplets of sample that may contaminate the outside of the device inlet 14. An operator then removes the device 10 which closes the self-closing inlet of the analyzer so that wash fluids may be circulated by the port without concern for leakage or aspiration of air. Importantly, the extended end cap shield 27 helps prevent an operator from contacting stent 24 which may be contaminated with sample.

Furthermore, when aspirating from the stent 24, there will be flow resistance as the plasma moves across the filter wall 44 through pores 42. Flow resistance is higher for plasma than it is for air. If the filter 30 were partially surrounded by blood and partially surrounded by air due to an incomplete fill, the fluidic circuit would be shorted out by the presence of the lower resistance air path. Accordingly, and as shown in FIGS. 2 and 4, the distribution of the pores 42 terminates towards the filter closed end 40 otherwise after separating a small amount of plasma air would contact the filter 30 and short out the plasma flow. Air should not contact the porous region of the filter 30 until all of the desired separated sample is produced. The device 10 produces a separated plasma volume no larger than about half the blood sample volume because the other half of the blood sample is blood cells. The amount of plasma removed from the sample will decrease the fill height and once the fill height is less than the height of the porous region of the filter 30, there will be no further separation. To obtain the maximum amount of plasma, the porous portion of the filter 30 should terminate at a height that corresponds to no more than the height of half of the initial blood fill volume.

An alternate embodiment of the present invention is shown in FIGS. 3 and 4. Rather than the flat cut profile as shown in FIG. 1 at the inlet 14, the device 10 has an angled cut at the inlet 14' with respect to the elongated tube 12 so as to produce a sharp projection 54. The projection 54 serves as a lancet for piercing a patient's skin for obtaining a small blood sample. Due to the self-filling nature of device 10, only a small amount of blood required to fill the device need be drawn from the patient, making the procedure of obtaining blood very fast and efficient.

Although the present invention has been described in considerable detail with reference to certain preferred versions, many other versions should be apparent to those skilled in the art. Therefore, the spirit and scope of the appended claims should not necessarily be limited to the description of the preferred versions contained herein.

What is claimed is:

1. A blood sampling device comprising:
   a hollow fluid tight tube having an inlet end defining an inlet chamber and an outlet end, the outlet end providing fluid exhaust from the interior of the tube; and
   a hollow fiber filter extending within and along a length of the tube, the filter being sealed at a first end thereof proximate to the inlet end and in fluid communication with the outlet end at a second end thereof, wherein
   the filter has a hollow interior and includes a plurality of pores sized to limit the passage of blood constituents from the inlet chamber to the interior of the filter, and to provide passage of blood plasma into the interior of the filter.

2. The device of claim 1, wherein the pores have diameters of about 2 micrometers.

3. The device of claim 2, wherein the pores are disposed along a length of the fiber filter from between the second end and a predetermined distance from the first end of said filter.

4. The device of claim 3 wherein the fiber filter has a cross section smaller than that of the inlet chamber defining thereby a fill volume there between.

5. The device of claim 4, wherein the predetermined distance is at a location that corresponds to no more than half of the fill volume.

6. The device of claim 1, wherein the pores have diameters in the range of about 0.1 to 1.0 micrometers.

7. The device of claim 1, wherein the inlet chamber defines (a) an inlet chamber wall having a wettable surface; and (b) a cross sectional area dimensioned such that the inlet chamber is self filling under the influence of capillary action.

8. The device of claim 7 wherein the inlet chamber contains an anticoagulant reagent to inhibit clotting.

9. The blood sampling device of claim 1 wherein at least one of the blood constituents is blood cells and the filter limits the passage of blood cells from the inlet chamber to the interior of the filter and allows the passage of blood plasma through the filter and into the hollow interior of the filter.

10. The blood sampling device of claim 1 wherein the device includes a hollow stent mounted to the fiber filter, the stent (a) extending from between the interior and exterior of the tube at the outlet end; and (b) providing an exhaust path from the interior of the filter.

11. A method of sampling blood comprising:
   a) selecting the device of claim 1;
   b) contacting the inlet end of the device with a blood sample;
   c) drawing the blood sample into the inlet chamber of the device;
   d) passing the blood plasma through the pores of the filter and into the interior of the filter, thereby separating the blood plasma from the blood sample; and
   e) withdrawing the blood plasma from the interior of the filter through the outlet end of the tube.

12. A method according to claim 11, wherein the blood sample is drawn into the inlet chamber by capillary action.

13. A method according to claim 11, wherein the blood plasma is withdrawn from the interior of the filter by inserting the device into the sampling port of an analyzer and aspirating the blood plasma through the outlet end of the tube and into the analyzer.

14. A blood sampling device comprising:
   a hollow fluid tight tube having an inlet defining an inlet chamber for receiving blood to be sampled and an outlet, the outlet providing fluid exhaust from the interior of the tube, said inlet chamber defining (a) an inlet chamber wall having a wettable surface; and (b) a cross sectional area dimensioned such that the inlet chamber is self filling under the influence of capillary action; and
   a blood separation filter positioned within the tube and adapted to separate blood elements from the blood and exhaust such separated blood elements through the outlet of the tube.

15. The blood sampling device of claim 14 wherein the separation filter comprises a hollow elongated fiber filter sealed at one end and coupled to the outlet at the other end, the filter having a hollow interior and a plurality of pores to provide a passageway for blood elements from the inlet chamber to the interior of the filter.

16. The blood sampling device of claim 15 wherein the pores are sized to limit the passage of blood cells to the interior of the filter and to provide passage of blood plasma into the interior of the filter.

17. The device of claim 16, wherein the pores have diameters of about 2 micrometers.

18. The device of claim 16, wherein the pores have diameters in the range of about 0.1 to 1.0 micrometers.

19. The blood sampling device of claim 14 wherein the outlet includes an end cap for providing a fluid tight seal of the outlet, the end cap including a hollow stent extending from between the interior and exterior of the tube at the outlet thereof, the stein in fluid communication with the filter to exhaust contents of the filter out of the device, and wherein the end cap further includes an outlet shield positioned to surround the outlet, the outlet shield dimensioned to extend beyond the stent so as to shield the stent against inadvertent contact by a user.

20. A blood sampling device comprising:
   a hollow fluid tight tube having an inlet end defining an inlet chamber and an outlet end; and
   a hollow fiber filter extending within and along a length of the tube, the filter being sealed at a first end thereof proximate to the inlet end and in fluid communication with the outlet end at a second end thereof, wherein
   the filter has a hollow interior and includes a plurality of pores sized so as to limit the passage of blood constituents from the inlet chamber to the interior of the filter and to provide passage of blood plasma into the interior of the filter, and
   the outlet end is distal to the inlet end and provides fluid exhaust from the interior of the filter.

21. A blood sampling device comprising:
   a hollow fluid tight tube having an inlet end defining an inlet chamber and an outlet end, wherein the outlet end provides fluid exhaust from the interior of the tube and includes an end cap for providing a fluid tight seal of the outlet end, the end cap including a hollow stent extending from between the interior and exterior of the tube at the outlet end; and
   a hollow fiber filter extending within and along a length of the tube, the filter being sealed at a first end thereof proximate to the inlet end and in fluid communication with the outlet end at a second end thereof, wherein
   the filter has a hollow interior and includes a plurality of pores sized so as to limit the passage of blood constituents from the inlet chamber to the interior of the filter and to provide passage of blood plasma into the interior of the filter.

22. The device of claim 21, wherein the fiber filter is mounted to the stent in a fluid tight seal fashion so as to provide a blood plasma exhaust path from the interior of the filter.

23. The device of claim 21, wherein the end cap includes an outlet shield positioned to surround the outlet, the outlet shield dimensioned to extend beyond the stent so as to shield the stent against inadvertent contact.

24. A blood sampling device comprising:
   a hollow fluid tight tube having (i) an inlet end defining an inlet chamber, the inlet end including a sharp projection adapted for piercing the skin of a patient, and (ii) an outlet end, the outlet end providing fluid exhaust from the interior of the tube; and
   a hollow fiber filter extending within and along a length of the tube, the filter being sealed at a first end thereof proximate to the inlet end and in fluid communication with the outlet end at a second end thereof, wherein
   the filter includes a plurality of pores sized so as to limit the passage of blood constituents from the inlet chamber to the interior of the filter and to provide passage of blood into the interior of the filter.

25. A blood sampling device comprising:

a hollow fluid tight tube having an inlet defining an inlet chamber for receiving blood to be sampled and an outlet, the outlet end providing fluid exhaust from the interior of the tube, said inlet chamber defining (a) an inlet chamber wall having a wettable surface; and (b) a cross sectional area dimensioned such that the inlet chamber is self filling under the influence of capillary action;

a hollow stent extending from between the interior and exterior of the tube at the outlet thereof; and a hollow blood separation filter positioned within the tube and adapted to separate blood elements from the blood and exhaust such separated blood elements through the hollow stent at the outlet of the tube.

26. A blood sampling device comprising:

a hollow fluid tight tube having an inlet defining an inlet chamber for receiving blood to be sampled and an outlet; and a blood separation filter positioned within the tube and adapted to separate blood elements from the blood and exhaust such separated blood elements through the outlet of the tube, wherein (a) the separation filter comprises a hollow elongated fiber filter sealed at one end and coupled to the outlet at the other end, the filter having a plurality of pores to provide a pssageway for blood elements from the inlet chamber to the interior of the filter;

(b) the outlet provides fluid exhaust from the interior of the tube and includes an end cap for providing a fluid tight seal of the outlet, the end cap including a hollow stent extending from between the interior and exterior of the tube at the outlet thereof, the stent in fluid communication with the filter to exhaust contents of the filter out of the device, and wherein the end cap further includes an outlet shield positioned to surround the outlet, the outlet shield dimensioned to extend beyond the stent so as to shield the stent against inadvertent contact by a user; and wherein (c) said inlet chamber defines (i) an inlet chamber wall having a wettable surface; and (ii) a cross sectional area dimensioned such that the inlet chamber is self filling under the influence of capillary action.

27. A blood sampling device comprising:

a hollow fluid tight tube having (a) an inlet defining an inlet chamber for receiving blood to be sampled and including a sharp projection adapted for piercing the skin of a patient, and (b) an outlet, the outlet providing fluid exhaust from the interior of the tube, wherein said inlet chamber defines (i) an inlet chamber wall having a wettable surface; and (ii) a cross sectional area dimensioned such that the inlet chamber is self filling under the influence of capillary action; and a blood separation filter positioned within the tube and adapted to separate blood elements from the blood and exhaust such separated blood elements through the outlet of the tube.

* * * * *